United States Patent [19]
Buckley

[11] Patent Number: 4,495,075
[45] Date of Patent: Jan. 22, 1985

[54] METHODS AND COMPOSITIONS FOR PREVENTING THE PRECIPITATION OF ZINC DIALKYLDITHIOPHOSPHATES WHICH CONTAIN HIGH PERCENTAGES OF A LOWER ALKYL GROUP

[75] Inventor: Thomas F. Buckley, Hercules, Calif.

[73] Assignee: Chevron Research Company, San Francisco, Calif.

[21] Appl. No.: 610,372

[22] Filed: May 15, 1984

[51] Int. Cl.[3] .................... C10M 1/48
[52] U.S. Cl. .................... 252/32.7 E; 252/389.21; 252/389 A
[58] Field of Search .................... 252/32.7 E, 389.21

[56] References Cited

U.S. PATENT DOCUMENTS

| | | | |
|---|---|---|---|
| 2,680,123 | 6/1954 | Mulvany | 252/32.7 E |
| 3,000,822 | 9/1961 | Higgins et al. | 252/32.7 E |
| 3,151,075 | 9/1964 | Butler | 252/32.7 E |
| 3,385,791 | 5/1968 | Colyer et al. | 252/32.7 E |
| 4,215,067 | 7/1980 | Brannen et al. | 260/429.9 |
| 4,306,984 | 12/1981 | Yamaguchi | 252/32.7 E |
| 4,443,360 | 4/1984 | Yamaguchi et al. | 252/32.7 E |

*Primary Examiner*—Helen M. McCarthy
*Assistant Examiner*—C. Johnson
*Attorney, Agent, or Firm*—S. R. LaPaglia; J. M. Whitney; G. F. Swiss

[57] ABSTRACT

Precipitation of a zinc dialkyldithiophosphate prepared from a mixture of about 50 to 90 mole percent of a lower alcohol plus 50 to 10 mole percent of a higher alcohol may be prevented by the addition to the composition of from about 0.5 to 10.0 percent by weight of an alkyl or alkenyl mono- or bis-succinimide.

14 Claims, No Drawings

METHODS AND COMPOSITIONS FOR PREVENTING THE PRECIPITATION OF ZINC DIALKYLDITHIOPHOSPHATES WHICH CONTAIN HIGH PERCENTAGES OF A LOWER ALKYL GROUP

BACKGROUND OF THE INVENTION

1. Field of the Invention

This invention pertains to novel zinc dialkyldithiophosphate compositions which are useful as anti-oxidant and anti-corrosion additives in a lubricant oil composition. In particular, this invention relates to zinc dialkyldithiophosphate compositions containing a high lower alkyl content. Said compositions contain from about 0.5 percent to 10 percent by weight of an alkyl or alkenyl mono- or bis-succinimide. The addition of the alkyl or alkenyl mono- or bis-succinimide substantially reduces the susceptibility of the zinc dialkyldithiophosphate compositions of this invention to form a precipitate, thus improving their solution stability.

2. Description of the Prior Art

Zinc salts of dialkyldithiophosphoric acids are known to inhibit the oxidation of the lubricant oil while improving the anti-corrosion property of the lubricant oil composition. It is also known that the alkyl groups of these zinc dialkyldithiophosphates may be of high molecular weight or low molecular weight. Zinc dialkyldithiophosphates wherein the alkyl groups are of four carbon atoms or less are considerably less expensive than the zinc dialkyldithiophosphates containing alkyl groups derived from alcohols having five or more carbon atoms. In spite of this, these zinc dialkyldithiophosphates containing only alkyl groups derived from alcohols having four or fewer carbon atoms have not been widely marketed as lubricating oil additives. Reasons for this have been that the zinc di(loweralkyl)dithiophosphates are insufficiently oil soluble to allow preparation of a concentrate. Moreover, the normally liquid compositions of the low molecular weight zinc dialkyldithiophosphates are prone to precipitation (crystallization).

Normally, the zinc dialkyldithiophosphate additives of this invention are oils and are transported either neat, that is only as the zinc dialkyldithiophosphate, or as a lubricating oil concentrate. In any event, precipitation of a portion of the additive during transport requires that the precipitate be solubilized prior to formulation.

In order to overcome this problem, U.S. Pat. Nos. 2,680,123; 3,151,075; 3,000,822; 3,385,791 and others teach the use of zinc dialkyldithiophosphates prepared from a mixture of a low molecular weight alcohol and a high molecular alcohol. This results in mixture of products containing a statistical distribution of pure zinc di(loweralkyl)dithiophosphate, zinc mixed-dialkyldithiophosphates and pure zinc di(higheralkyl)dithiophosphate as shown in the formula below:

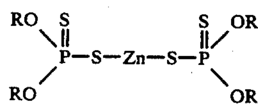

I wherein R may be either a lower or higher alkyl group.

The use of the mixed alcohols improves the oil solubility of the resulting product while also lowering its overall costs.

However, as the percent by mole ratio of the lower alcohol to the total alcohol employed in preparing the mixed dialkyldithiophosphate exceeds approximately 50 percent, problems with the solution stability of the resulting zinc dialkyldithiophosphate composition are again raised. This problem results in a precipitate forming in the zinc dialkyldithiophosphate solutions. This problem of precipitation in zinc dialkyldithiophosphates of high lower alkyl content is most apparent when the lower alkyl methyl, ethyl, n-propyl and isopropyl groups are employed but also arises when isomers of butyl alcohol are employed. This is particularly evident when the amount of butyl alcohol used to form the zinc dialkyldithiophosphate is raised to approximately 75 to 90 percent of the total alcohol content.

Without being limited to any particular theory, it is believed that, as the level of the lower alcohol employed to form the zinc dialkyldithiophosphate is raised, the statistical distribution of products favors greater amounts of pure zinc di(loweralkyl)dithiophosphate (wherein all the R groups in FIG. 1 are the same lower alkyl group). These pure zinc di(loweralkyl)dithiophosphates are known to be prone to crystallization in solution and to be both insoluble in oil. Thus, although the use of a lower alcohol is economically favorable, the use of increasing amounts of the lower alcohol results in solubility and crystallinity problems in the product.

Accordingly, the use of a mixture of lower and higher alcohols in preparing zinc dialkyldithiophosphates is limited to mole ratios of lower to higher alcohols which favor a low statistical proportion of pure zinc di(-loweralkyl)dithiophosphate. Nevertheless, the use of a maximum amount of the lower alcohol is economically advantageous and thus a solution which alleviates the problems of precipitation and solubility associated with the use of large amounts of the lower alcohol would be particularly beneficial.

This invention is directed to zinc dialkyldithiophosphate compositions of high lower alkyl content which are not prone to precipitation under normal storage conditions.

Yamaguchi, in U.S. Pat. No. 4,306,984 as well as in U.S. Ser. No. 437,371, discloses that oil insoluble salts of diloweralkyldithiophosphoric acid may be solubilized by complexing these salts with from 3:1 to 10:1 weight ratio of an alkenyl or alkyl mono- or bis-succinimide.

Likewise, Yamaguchi et al., in U.S. Pat. No. 4,443,360 as well as in pending U.S. Ser. No. 443,362, disclose that oil insoluble salts of cycloalkyldithiophosphoric acid may be solubilized by complexing these salts with from 3:1 to 25:1 weight ratio of an alkenyl or alkyl mono- or bis-succinimide.

I have now found that precipitation (crystallization) of zinc dialkyldithiophosphate compositions prepared from the reaction of phosphorus pentasulfide with a mixture of about 50 to 90 mole percent of a lower alcohol plus 50 to 10 mole percent of a higher alcohol followed by the neutralization of the resulting dialkyldithiophosphoric acid with a basically reacting zinc compound may be alleviated by the addition to the composition of about from 0.5 to about 10.0 percent by weight of an alkyl or alkenyl mono- or bis-succinimide. This is particularly surprising in view of the large excess of succinimide required by Yamaguchi and Yamaguchi et al. to prepare an oil-soluble zinc dithiophosphate complex.

This surprising result of this invention is particularly advantageous as the smaller amount of succinimide required in the zinc dialkyldithiophosphate composition results in concentrates of less bulk and, accordingly, easier and cheaper transportation.

SUMMARY OF THE INVENTION

In its composition aspect, the present invention is drawn to an anti-oxidant, anti-corrosion zinc dialkyldithiophosphate composition which is stable to precipitation which comprises:

(a) a zinc dialkyldithiophosphate prepared from the reaction of phosphorus pentasulfide with a mixture of about 50 to 90 percent of a lower alcohol plus about 50 to 10 percent of a higher alcohol followed by neutralization of the resulting dialkyldithiophosphoric acid with a basically reacting zinc compound; and (b) about 0.1 to 10.0 percent by weight of an oil-soluble alkenyl or alkyl mono- or bis-succinimide of the formula:

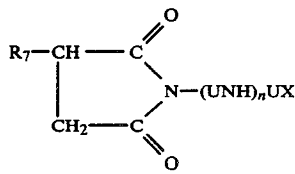

wherein X is amino or a group of the formula:

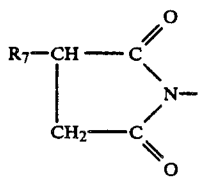

$R^7$ is an alkenyl or alkyl group containing from about 20 to 60 carbon atoms; U is alkylene containing from 2 to 6 carbon atoms; and n is an integer of from 0 to 6.

In its method aspect, the present invention is drawn to a method of preventing precipitation in a zinc dialkyldithiophosphate composition prepared from reacting phosphorus pentasulfide with a mixture of about 50 to 90 mole percent of a lower alcohol and 50 to 10 percent of a higher alcohol followed by neutralization of the resulting dialkyldithiophosphoric acid with a basically reacting zinc compound which comprises the addition to the said zinc composition of about 0.5 percent to about 10.0 percent by weight of an alkyl or alkenyl mono- or bis-succinimide of the formula:

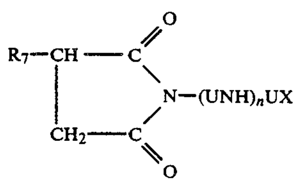

wherein X is amino or a group of the formula:

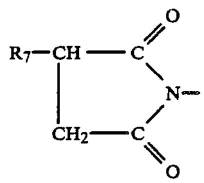

$R^7$ is an alkenyl or alkyl group containing from about 20 to 60 carbon atoms; U is alkylene containing 2 to 6 carbon atoms; and n is an integer of from 0 to 6.

Preferably, about 0.5 to 5.0 percent by weight of the alkyl or alkenyl mono- or bis-succinimide is added to the composition. Most preferably, about 1.0 to 5.0 percent by weight of the alkyl or alkenyl mono- or bis-succinimide is added to the composition.

Preferred zinc dialkyldithiophosphates are those prepared by reacting phosphorus pentasulfide with a mixture of about 60 to 80 mole percent of a lower alcohol plus 40 to 20 mole percent of a higher alcohol followed by neutralization of the resulting dialkyldithiophosphoric acid with a basically reacting zinc compound such as zinc oxide.

A particularly preferred lower alcohol used in preparing the zinc dialkyldithiophosphates is isopropanol. A particularly preferred higher alcohol is 2-ethylhexanol.

In a preferred aspect of the present invention, the zinc dialkyldithiophosphate is prepared from a mixture of 70 mole percent of isopropanol/30 mole percent of 2-ethylhexanol.

Preferred succinimides of this invention are the alkyl or alkenyl mono-succinimide prepared by reacting an alkyl or alkenyl succinic anhydride with either tetraethylene pentamine or with triethylene tetramine. Most preferably, tetraethylene pentamine is employed.

As employed herein, the following terms have the following meaning unless expressly stated to the contrary.

The term "zinc dialkyldithiophosphate" means zinc dialkyldithiophosphates prepared from the reaction of phosphorus pentasulfide (or its equivalent) with a mixture of from 50 to 90 percent of a lower alcohol and from 50 to 10 percent of a higher alcohol followed by neutralization of the resulting dialkyldithiophosphoric acid with a basically reacting zinc compound.

The term "prevent(ing) the precipitation of zinc dialkyldithiophosphates" does not mean that precipitation will be prevented under all conditions but refers to the retardation of precipitation at normal storage conditions of about 0°-50° C. for a period of up to 6 months.

The term "lower alcohol" means alcohols having four or fewer carbon atoms and includes for instance ethanol, n-propanol, isopropanol, n-butanol, isobutanol, sec-butanol and t-butanol.

The term "higher alcohol" means alcohols having 5 to 18 carbon atoms and includes for instance n-pentanol, n-hexanol, 2-ethylhexanol, n-decanol, and the like.

It will be understood that in the context of this invention other salts of zinc dialkyldithiophosphate may be considered as substitutes for zinc. Examples of such salts are the nickel salts, barium salts, copper salts, magnesium salts, sodium salts, calcium salts, and the like.

Likewise, other phosphorus sulfides may be employed as substitutes for phosphorus pentasulfide and are considered as equivalent of phosphorus pentasulfide, such phosphorus sulfides includes $P_5S_7$, $P_4S_8$, etc. However, for reasons of low cost reactivity and availability, phosphorus pentasulfide ($P_2S_5$) is preferred.

DETAILED DESCRIPTION OF THE INVENTION

The compositions of this invention may be conveniently prepared by adding the desired amount of an alkyl or alkenyl mono- or bis-succinimide to the zinc dialkyldithiophosphate.

Generally, the zinc dialkyldithiophosphate is prepared by first preparing the dialkyldithiophosphoric acid and then neutralizing this acid with a basically reacting zinc compound. The dialkyldithiophosphoric acid may be prepared by the addition to phosphorus pentasulfide of four equivalents (or a slight excess thereof) of the alcohol (which is a mixture of a lower and a higher alcohol) as shown below:

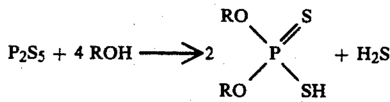

wherein R is a mixture of lower alkyl (4 carbons or less) and higher alkyl (5 to 18 carbons). The dialkyldithiophosphoric acid is then neutralized by the addition of 1.0 to 1.5 equivalents of a basically reacting zinc compound, optionally in the presence of a polar promoter such as water, acetic acid, nitric acid, ammonium acetate, and the like.

Preferably, the pH of the resulting zinc dialkyldithiophosphate should be maintained between pH 5.5 and 7.0 and most preferably between 6.0 and 6.5. Normally, the pH of the resulting zinc composition is controlled by controlling the amount of excess of the basically reacting zinc compound employed.

The oil-soluble alkenyl or alkyl mono- or bis-succinimide which are employed in the additive combination of this invention are generally known as lubricating oil detergents and are described in U.S. Pat. Nos. 2,992,708; 3,018,291; 3,024,237; 3,100,673; 3,219,666; 3,172,892; and 3,272,746, the disclosures of which are incorporated by reference. These materials are prepared by reacting an alkyl or alkyl-substituted succinic anhydride of the formula:

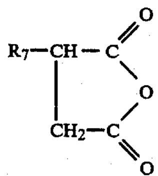

wherein $R_7$ is an alkenyl or alkyl group containing from about 10 to 60 carbon atoms, with a polyalkylene polyamine of the formula:

$$H_2N\text{-}(UNH)_nUNH_2$$

wherein U is alkylene of 2 to 6 carbons and n is an integer of 0 to 6.

The alkylene group designated by U, which contains from 2 to 6 carbon atoms, may be straight chained or branched, but will usually be straight chained. Illustrative alkylene groups are ethylene, propylene, 1,2-propylene, tetramethylene, hexamethylene, etc. The preferred alkylene groups are from 2 to 3 carbon atoms, there being 2 carbon atoms between the nitrogen atoms.

Non-limiting examples of suitable amino compounds include: 1,2-diaminoethane; 1,3-diaminopropane; 1,4-diaminobutane; 1,6-diaminohexane; diethylene triamine; triethylene tetramine; tetraethylene pentamine; 1,2-propylene diamine; and the like.

A product comprising predominantly mono- or bis-succinimide can be prepared by controlling the molar ratios of the reactants. Thus, for example, if 1 mole of amine is reacted with 1 mole of the alkenyl or alkyl-substituted succinic anhydride, a predominantly mono-succinimide product will be prepared. If 2 moles of the succinic anhydride are reacted per mole of polyamine, a bis-succinimide will be prepared.

The preparation of the alkenyl-substituted succinic anhydride by reaction with a polyolefin and maleic anhydride has been described, e.g., U.S. Pat. Nos. 3,018,250 and 3,024,195. Reduction of the alkenyl-substituted succinic anhydride yields the corresponding alkyl derivative. Polyolefin polymers for reaction with the maleic anhydride are polymers comprising a major amount of $C_2$ to $C_5$ mono-olefin, e.g., ethylene, propylene, butylene, isobutylene, and pentene. The polymers can be homopolymers such as polyisobutylene as well as copolymers of 2 or more such olefins such a copolymers of: ethylene and propylene, butylene, and isobutylene, etc. Other copolymers include those in which a minor amount of the copolymer monomers, e.g., 1 to 20 mole percent is a $C_4$ to $C_8$ nonconjugated diolefin, e.g., a copolymer of isobutylene and butadiene or a copolymer of ethylene, proplene, and 1,4-hexadiene, etc.

The olefin polymers contain from about 20 to 300 carbon atoms and preferably from 20 to 60 carbon atoms. An especially preferred polyolefin is polyisobutylene.

The zinc dialkyldithiophosphate plus alkyl or alkenyl mono- or bis-succinimide compositions of this invention are useful as anti-oxidant and anti-corrosion additives in lubricating oils. When employed in this manner, the zinc dialkyldithiophosphate compositions are usually present in from 0.1 to 4.0 percent by weight to the total composition and perferably at about 1 percent by weight. The lubricating oil used with the additive compositions of this invention may be mineral oil or synthetic oils of lubricating viscosity and preferably suitable for use in the crankcase of an internal combustion engine. Crankcase lubricating oils ordinarily have a viscosity of about 1300 cst 0° F. to 22.7 cst at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Additive concentrates are also included within the scope of this invention. Concentrates of zinc dialkyldithiophosphate are prone to precipitation or haziness when the lower alkyl content is raised above 50 mole percent. However, concentrates of the zinc dialkyldithiophosphate-succinimide compositions of the instant invention are not prone to precipitation or haziness. The concentrates of this invention usually include from about 50 to 10 weight percent of an oil of lubricating viscosity and from about 50 to 90 weight percent of the complex additive of this invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although an oil of lubricating viscosity may be used.

Other additives which may be present in the formulation include rust inhibitors, foam inhibitors, corrosion inhibitors, metal deactivators, pour point depressants, antioxidants, and a variety of other well-known additives.

EXAMPLES

Example 1

Preparation of Zinc Isopropyl-2-Ethylhexyl Dithiophosphate

Prepare a 70/30 mole ratio mixture of isopropanol to 2-ethylhexanol by mixing 544 gm of isopropanol and 506 gm of 2-ethylhexanol. Add 350 gm of this mixture to a three liter three neck round bottom flask equipped with a mechanical stirrer and with a venting system to a 25 percent sodium hydroxide scrubber. Add phosphorus pentasulfide (732 gm) to the system in portions over a period of time. Since this addition is exothermic, maintain the system during addition at approximately 71° C. by an external ice-water bath. To the stirred slurry, add an additional 700 gm of the isopropanol/2-ethylhexanol mixture to the system over approximately 2 hours while maintaining the temperature of the system at 71° C. Stir the system for an additional 5 hours at 71° C. and then cool to approximately 54° C. Suction filter the product through paper and then sparge it with nitrogen to give the isopropyl-2-ethylhexyldithiophosphoric acid having a total acid number (TAN) of 205.

Add isopropyl-2-ethylhexyldithiophosphoric acid (91.2 gm) to a three neck round bottom flask equipped with a mechanical stirrer. Add 46.6 gm of zinc oxide (1.15 equivalents based upon the TAN of the total dithiophosphoric acid employed) to the system. Hold the temperature at approximately 71° C. and add an additional 182.8 gm of the isopropyl-2-ethylhexyldithiophosphoric acid to the system. Maintain the temperature of 71° C. for an additional 4 hours. Add 15.6 gm of polyisobutenyl succinimide, prepared by reacting 1 equivalent of polyisobutenyl succinic anhydride of approximately 1,000 average molecular weight with tetraethylene pentamine, to the system and stir this mixture at 71° C. for an additional hour. Strip the water under reduced pressure at 71° C. for 30 minutes. Add celite and filter to give the titled product containing an effective amount of polyisobutenyl succinimide to prevent precipitation or crystallization of the titled product.

Example 2

Alternate Preparation of Zinc Isopropyl-2-Ethylhexyl Dithiophosphate

Add isopropyl-2-ethylhexyldithiophosphoric acid (274 gm with a TAN of 205) to a three neck round bottom flask equipped with a mechanical stirrer. Add 46.6 gm of zinc oxide (1.15 equivalents based upon the TAN of the total dithiophosphoric acid employed) to the system. Hold the temperature at approximately 71° C. for 2 hours. Add 15.2 gm of a polyisobutenyl succinimide, prepared by reacting 1 equivalent of polyisobutenyl succinic anhydride of approximately 1,000 average molecular weight with tetraethylene pentamine, to the system and stir at 71° C. for 1 hour. Strip the water from the system under reduced pressure at 71° C. for 30 minutes. Add celite and filter to give the title compound containing an effective amount of polyisobutenyl succinimide to prevent precipitation or crystallization of the titled product.

Example 3

Alternatively, the succinimide may be added after stripping and filtration of the zinc dialkyldithiophosphate.

A sample of a zinc dialkyldithiophosphate was prepared from a mixture of about 70 mole percent isopropanol plus about 30 mole percent 2-ethylhexanol in a manner similar to that shown in Example 1, but without the addition of the polyisobutenyl succinimide. Upon standing this composition formed a precipitate.

Example 4

Alternatively, the succinimide may be added at any stage of the reaction. Preferably, the succinimide is present in the reaction system prior to the addition of the basically reacting zinc compound.

What is claimed is:

1. An anti-oxidant anti-corrosion zinc dialkyldithiophosphate composition which is stable to precipitation which comprises:

(a) a zinc dialkyldithiophosphate prepared from the reaction of phosphorus pentasulfide with a mixture of about 50 to 90 percent of a lower alcohol plus about 50 to 10 percent of a higher alcohol followed by neutralization of the resulting dialkyldithiophosphoric acid with a basically reacting zinc compound; and (b) about 0.1 to 10.0 percent by weight to the zinc dialkyldithiophosphate of an oil-soluble alkenyl or alkyl mono- or bis-succinimide of the formula:

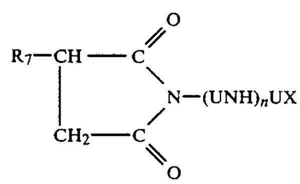

wherein X is amino or a group of the formula:

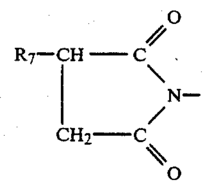

$R_7$ is an alkenyl or alkyl group containing from about 20 to 60 carbon atoms; U is alkylene containing 2 to 6 carbon atoms; and n is an integer of from 0 to 6.

2. The composition of claim 1 wherein said lower alcohol is isopropanol and said higher alcohol is 2-ethylhexanol.

3. The composition of claim 2 wherein said zinc dialkyldithiophosphate is prepared from an alcohol mixture comprising about 70 mole percent isopropanol and about 30 mole percent 2-ethylhexanol.

4. The composition of claim 3 wherein n in said alkenyl or alkyl mono- or bis-succinimide is 2 or 3.

5. The composition of claim 4 wherein U is ethylene and X is amino.

6. The composition of claim 4 wherein U is ethylene and X is a group of the formula:

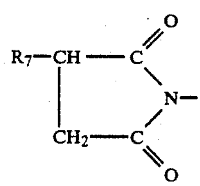

wherein $R_7$ is an alkenyl or alkyl group containing from about 20 to 60 carbon atoms.

7. A method of preventing precipitation in a zinc dialkyldithiophosphate composition prepared from reacting phosphorus pentasulfide with a mixture of about 50 to 90 mole percent of a lower alcohol and 50 to 10 mole percent of a higher alcohol followed by neutralization of the resulting dialkyldithiophosphoric acid with a basically reacting zinc compound which comprises the addition of about 0.5 percent to about 10.0 percent by weight to the zinc dialkyldithiophosphate of an alkyl or alkenyl mono- or bis-succinimide of the formula:

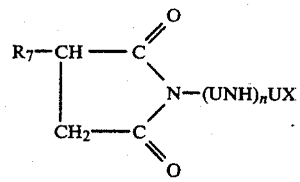

wherein X is amino or a group of the formula:

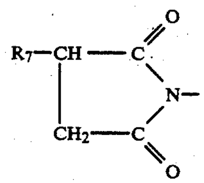

$R_7$ is an alkenyl or alkyl group containing from about 20 to 60 carbon atoms; U is alkylene containing 2 to 6 carbon atoms; and n is an integer of from 0 to 6.

8. The method of claim 7 wherein said lower alcohol is isopropanol and said higher alcohol is 2-ethylhexanol.

9. The method of claim 8 wherein said zinc dialkyldithiophosphate is prepared from an alcohol mixture comprising about 70 mole percent isopropanol and about 30 mole percent 2-ethylhexanol.

10. The method of claim 9 wherein n in said alkenyl or alkyl mono- or bis-succinimide is 2 or 3.

11. The method of claim 9 wherein U is ethylene and X is amino.

12. The method of claim 9 wherein U is ethylene and X is a group of the formula:

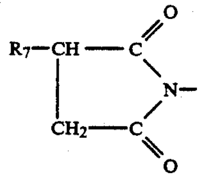

wherein $R_7$ is an alkenyl or alkyl group containing from about 20 to 60 carbon atoms.

13. A lubricating oil concentrate comprising a minor amount of an oil of lubricating viscosity and a major amount of an anti-oxidant anti-corrosion composition of claim 1.

14. A lubricating oil concentrate comprising a minor amount of an oil of lubricating viscosity and a major amount of an anti-oxidant anti-corrosion composition of claim 5.

* * * * *